(12) United States Patent
Bensimon et al.

(10) Patent No.: US 9,738,928 B2
(45) Date of Patent: *Aug. 22, 2017

(54) METHOD OF DNA SEQUENCING BY POLYMERISATION

(71) Applicants: ECOLE NORMALE SUPERIEUR, Paris (FR); CENTRE NATIONAL DE LA RECHERCHE SCIENTIFIQUE (CNRS), Paris (FR); UNIVERSITE PIERRE ET MARIE CURIE (PARIS 6), Paris (FR)

(72) Inventors: David Bensimon, Paris (FR); Vincent Croquette, Antony (FR); Jean-Francois Allemand, Arcueil (FR); Maria Manosas, Barcelona (ES); Fang-Yuan Ding, Paris (FR)

(73) Assignees: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/334,593

(22) Filed: Oct. 26, 2016

(65) Prior Publication Data
US 2017/0073749 A1    Mar. 16, 2017

Related U.S. Application Data

(63) Continuation of application No. 13/700,115, filed as application No. PCT/EP2011/058664 on May 26, 2011, now Pat. No. 9,493,829.
(Continued)

(30) Foreign Application Priority Data

May 27, 2010   (EP) .................... 10305563

(51) Int. Cl.
*C12P 19/34*    (2006.01)
*C12Q 1/68*    (2006.01)
(Continued)

(52) U.S. Cl.
CPC ......... *C12Q 1/6869* (2013.01); *C12Q 1/6874* (2013.01)

(58) Field of Classification Search
USPC ............ 435/6.1, 6.11, 6.12, 91.1, 91.2, 183, 435/283.1, 287.1, 287.2; 436/94, 501;
(Continued)

(56) References Cited

U.S. PATENT DOCUMENTS 4,849,077 A   7/1989   Rosenthal et al.
4,882,127 A   11/1989   Rosenthal et al.
(Continued)

FOREIGN PATENT DOCUMENTS

EP   1141399 B1   10/2001
WO   03066896 A2   8/2003
(Continued)

OTHER PUBLICATIONS

Cloonan et al, Nat. Methods. 2008;5(7):613-619.
(Continued)

*Primary Examiner* — Frank Lu
(74) *Attorney, Agent, or Firm* — Arrigo, Lee & Guttman LLP (57) ABSTRACT

The present invention relates to a method for the determination of a nucleic acid sequence by physical manipulation. The method is based on the precise determination of the localization of the replicating fork on the template by measuring the physical distance between one end of the molecule and the fork. This allows the determination of the physical location of the site where a pause or a blockage of
(Continued)

the replication occurs, and deducing therefrom information on the sequence of the nucleic acid.

13 Claims, 5 Drawing Sheets

Related U.S. Application Data

(60) Provisional application No. 61/377,621, filed on Aug. 27, 2010.

(51) Int. Cl.
*C07H 21/02* (2006.01)
*C07H 21/04* (2006.01)
*C07H 21/00* (2006.01)

(58) Field of Classification Search
USPC .......................... 536/23.1, 24.3, 24.33, 25.3
See application file for complete search history.

(56) References Cited

U.S. PATENT DOCUMENTS

| | | | |
|---|---|---|---|
| 6,723,513 | B2 | 4/2004 | Lexow |
| 7,556,922 | B2 | 7/2009 | Block et al. |
| 9,493,829 | B2 * | 11/2016 | Bensimon ............ C12Q 1/6874 |
| 2003/0027187 | A1 | 2/2003 | Strick et al. |
| 2003/0166232 | A1 | 9/2003 | Saras et al. |
| 2003/0166262 | A1 | 9/2003 | Strick et al. |
| 2006/0275782 | A1 | 12/2006 | Gunderson et al. |
| 2008/0020392 | A1 | 1/2008 | Block et al. |
| 2009/0181385 | A1 | 7/2009 | Mckernan et al. |
| 2009/0181860 | A1 | 7/2009 | Mckernan et al. |
| 2009/0186349 | A1 | 7/2009 | Gunderson et al. |
| 2010/0035252 | A1 | 2/2010 | Rothberg et al. |
| 2013/0137098 | A1 | 5/2013 | Bensimon et al. |
| 2013/0171636 | A1 | 7/2013 | Bensimon et al. |
| 2015/0031028 | A1 | 1/2015 | Bensimon et al. |

FOREIGN PATENT DOCUMENTS

| | | |
|---|---|---|
| WO | 2006084132 A2 | 8/2006 |
| WO | 2007111924 A2 | 10/2007 |
| WO | 2010016937 A2 | 2/2010 |

OTHER PUBLICATIONS

Fuller et al., Nature Biotechnol. 2009;27(11)1013-1023.
Hutchinson, Nucl. Acids Res. 2007;35(18):6227-6237.
Maier et al, Proc Natl Acad Sci U.S.A. 2000;97(22):12002-12007.
Walter et al, Proc Natl Acad Sci U.S.A., 2009;106(31):12950-12955.
Shendure et al., Nature Biotechnol. 2008:26(10)1135-1145.
International Search Report for PCT/EP2011/058664 Mailed July 20, 2011.
Ding et al, Single Molecule mechanical identification and sequencing, Nature Method, 9, 367-372, 2012.
Manosas et al., Mechanism of strand displacement synthesis by DNA replicative polymerases, Nucleic Acids Research, 2012, 40:6174-6186.

\* cited by examiner

\*
GGATTCGCGGGTCTCTTCCTGATTGTCATCGGCTGGCTGTTCGGTTAGTTTCGAAGACTTTCGCC
TGATCGTCCACT (SEQ ID NO: 5)

```
                              SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1
aactgaccaa acgtcggtgg g                                                 21

<210> SEQ ID NO 2
<211> LENGTH: 16
<212> TYPE: DNA
<213> ORGANISM: Artificial Sequence
<220> FEATURE:
<223> OTHER INFORMATION: Hairpin stem sequence

<400> SEQUENCE: 2
ggattcgcgg gtctct                                                       16

<210> SEQ ID NO 3
<211> LENGTH: 42
<212> TYPE: DNA
<213> ORGANISM: Artificial Sequence
<220> FEATURE:
<223> OTHER INFORMATION: Hairpin loop sequence
<220> FEATURE:
<221> NAME/KEY: misc_feature
<222> LOCATION: (20)..(20)
<223> OTHER INFORMATION: n stands for a base abasic
<220> FEATURE:
<221> NAME/KEY: misc_feature
<222> LOCATION: (22)..(22)
<223> OTHER INFORMATION: n stands for a base abasic
<220> FEATURE:
<221> NAME/KEY: misc_feature
<222> LOCATION: (24)..(24)
<223> OTHER INFORMATION: n stands for a base abasic
<220> FEATURE:
<221> NAME/KEY: misc_feature
<222> LOCATION: (26)..(26)
<223> OTHER INFORMATION: n stands for a base abasic

<400> SEQUENCE: 3
tcgcgcctga tcgtccactn tntntntagt ggacgatcag gc                          42

<210> SEQ ID NO 4
<211> LENGTH: 41
<212> TYPE: DNA
<213> ORGANISM: Artificial Sequence
<220> FEATURE:
<223> OTHER INFORMATION: Hairpin stem sequence

<400> SEQUENCE: 4
aggaagagac ccgcgaatcc cccaccgacg tttggtcagt t                           41

<210> SEQ ID NO 5
<211> LENGTH: 77
<212> TYPE: DNA
<213> ORGANISM: Artificial Sequence
```

-continued

```
<220> FEATURE:
<223> OTHER INFORMATION: artificial nucleic acid sequence derived from
      the method of the instant invention

<400> SEQUENCE: 5
ggattcgcgg gtctcttcct gattgtcatc ggctggctgt tcggttagtt tcgaagactt    60
tcgcctgatc gtccact                                                   77
```

METHOD OF DNA SEQUENCING BY POLYMERISATION

The present invention relates to a fast method for the determination of a sequence of a nucleic acid, DNA or RNA, which is useful, in particular, for the sequencing of an unknown nucleic acid or alternatively for the detection of a specific nucleic acid sequence for diagnosis.

Nowadays, the determination of nucleic acid sequence is at the heart of molecular biology. For example, a broad range of biological phenomena can be assessed by high-throughput DNA sequencing, e.g., genetic variation, RNA expression, protein-DNA interactions and chromosome conformation (see, for a few examples, Mitreva & Mardis, *Methods Mol Biol.*, 533: 153-87, 2009; Mardis, *Genome Med.*, 1(4): 40, 2009; Cloonan et al., *Nat Methods*, 5(7): 613-619, 2008; Valouev et al., *Genome Res.*, 18(7):1051-63, 2008, Valouev et al., *Nat Methods.*, 5(9):829-34, 2008; Orscheln et al., *Clin Infect Dis.*, 49(4): 536-42, 2009 ; Walter et al., *Proc Natl Acad Sci USA.*, 106(31): 12950-5, 2009; Mardis et al., *N Engl J Med.*, 361(11): 1058-66, 2009, Hutchinson, *Nucl. Acids Res.*, 35(18): 6227-6237, 2007).

In addition, demonstration of the presence of a specific DNA sequence in a physiological sample constitutes, at the present time, the major line of development of diagnostic methods, e.g. for identifying the probability of bacteria of developing antibiotic resistance, genetic abnormalities, the risks of cancer associated with genetic modifications and viral infections, for example infections associated with HIV or with hepatitis viruses (see for example Zhang et al., *Nature*, 358: 591-593, 1992; Turner et al., *J Bacteriol*, 176(12): 3708-3722, 1994; Weston et al., *Infection and Immunity*, 77(7): 2840-2848, 2009).

Nucleic acid sequencing is nowadays carried out chiefly with capillary-based, semi-automated implementations of the Sanger biochemistry. The classical method comprises a step of amplification of the DNA of interest, followed by a step of 'cycle sequencing', wherein each round of primer extension is stochastically terminated by the incorporation of fluorescently labeled dideoxynucleotides (ddNTPs). Sequence is determined by high-resolution electrophoretic separation of the single-stranded, end-labelled extension products in a capillary-based polymer gel. Simultaneous electrophoresis in 96 or 384 independent capillaries provides a limited level of parallelization.

The high demand for low-cost sequencing has driven the development of high-throughput sequencing technologies that parallelize the sequencing process, producing thousands or millions of sequences at once (Shendure & Ji, *Nat Biotechnol.*, 26(10): 1135-45. 2008). High-throughput sequencing technologies are intended to lower the cost of DNA sequencing beyond what is possible with standard dye-terminator methods. At present this very high throughput is achieved with substantial sacrifices in length and accuracy of the individual reads when compared to Sanger sequencing. Examples of such new methods include the 454 and the Solexa technologies. These technologies allow shotgun sequencing of whole genomes without cloning in *E. coli* or any host cell. Libraries of short, adaptor-flanked DNA fragments captured on the surface of beads are amplified by emulsion PCR. Sequencing is carried out using primed synthesis by DNA polymerase. In the 454 method (also known as 'pyrosequencing'), the array is presented with each of the four dNTPs, sequentially, and the amount of incorporation is monitored by luminometric detection of the pyrophosphate released. A key difference between this method and the Solexa is that the latter uses chain-terminating nucleotides. The fluorescent label on the terminating base can be removed to leave an unblocked 3' terminus, making chain termination a reversible process. The SOLiD technology relies on the ligation of fluorescently labeled di-base probes to a sequencing primer hybridized to an adaptor sequence within the clonally-amplified library template. Specificity of the di-base probe is achieved by interrogating every 1st and 2nd base in each ligation reaction. Multiple cycles of ligation, detection and cleavage are performed with the number of cycles determining the eventual read length. In contrast to the three previous technologies, which all require a first step of amplification, the Helicos platform allows the sequencing of single DNA molecules. This technology is based on the use of a highly sensitive detection system of fluorescent nucleotides incorporation to directly interrogate single DNA molecules via sequencing by synthesis.

Such methods are described in e.g. U.S. Pat. Nos. 4,882,127, 4,849,077; 7,556,922; 6,723,513; PCT Patent Application No. WO 03/066896; PCT Patent Application No. WO2007111924; U.S. Patent Application No. US 2008/0020392; PCT Patent Application No. WO 2006/084132; U.S. Patent Application No. US 2009/0186349; U.S. Patent Application No. US 2009/0181860; U.S. Patent Application No. US 2009/0181385; U.S. Patent Application No. US 2006/0275782; European Patent EP-B1-1141399; Shendure & Ji, *Nat Biotechnol.*, 26(10): 1135-45. 2008; Pihlak et al., *Nat Biotechnol.*, 26(6) : 676- 684, 2008; Fuller et al., *Nature Biotechnol.*, 27(11): 1013-1023, 2009; Mardis, *Genome Med.*, 1(4): 40, 2009; Metzker, *Nature Rev. Genet.*, 11(1): 31-46, 2010.

However, all the methods developed so far suffer from serious drawbacks. In particular, they all make use of labelled nucleotides (e.g. fluorescent), thus contributing to seriously increasing the overall costs. Moreover, all these new methods bar one (the Helicos platform) require amplification of the target sequence prior to sequencing, which is time consuming on the one hand, increases the probability of errors on the other hand, and is highly prone to contamination. In addition, the methods involving mechanical techniques rather than biochemical lack sensitivity (Maier et al., *Proc. Natl., Acad. Sci. U.S.A.*, 97(22): 12002-12007, 2000; Wuite et al., *Nature*, 404(6773): 103-106, 2000; US 2010/0035252) There is thus still a need for new, highly sensitive method allowing the sequencing of single molecules.

DETAILED DESCRIPTION OF THE INVENTION

The present invention relates to a method for the determination of a nucleic acid sequence by physical manipulation. In particular, the said method comprises the steps of determining the physical location of the site where a pause of the replication occurs, and deducing there-from information on the sequence of the nucleic acid.

The method according to the present invention, based on physical techniques and electronic treatments, differs from the current approaches, which are chemical or biochemical. Its advantages are numerous:

1) It allows the sequencing of a single molecule, and thus does not require a previous amplification step (e.g. by PCR).
2) It is far cheaper than the methods of the art since standard nucleic acid molecules are used, which are far less expensive than labelled nucleotides (either with fluorophores or some other groups).

3) It enables to determine the localization (in bp) of a newly synthesized complementary strand along a double stranded nucleic acid by measuring the distance between the two ends of the said double-stranded nucleic acid molecule.
4) In one embodiment it allows in one polymerization run to determine the position of a given nucleotide along the strand.
5) The measurement can be repeated periodically on a second time-scale, thus leading to elimination of false positives (spurious arrest of the polymerase), improved statistics and a significant reduction in instrumental drifts.
6) The experiment can be repeated many times on the same molecule, thus improving the statistics and the reliability of the measurement, since the newly synthesized single stranded nucleic acid can be ejected (by e.g. reducing the force or the ionic strength or by using a helicase or an exonuclease activity) after the replication step. It allows for the parallel sequencing of various double-stranded nucleic acid molecules, since each molecule can be manipulated independently of the others.
7) A non-modified enzyme can be used to sythesize the new strand, which lowers the associated costs and improves the error rate, as compared to the third-generation single molecule sequencing, which either introduces site-specific mutation in the polymerase to cleave the dye-linker, or binds the enzyme to a side, or modifies it with a quantum dot.

The present invention relates to a method for the determination of a nucleic acid sequence based on the physical localization on the sequenced nucleic acid molecule of the sites where replication is paused or blocked.

By 'determination of a nucleic acid sequence', it is herein meant not only the deciphering of the actual succession of bases in a nucleic acid, but also all the activities leading directly or indirectly to the obtention of some information on nucleic acid sequence, such as the detection of a particular sequence in a nucleic acid molecule or the detection of a difference between the sequences of two different nucleic acid molecules.

Most methods for determining a nucleic acid sequence rely on primed synthesis of a new strand by a processive polymerase. In these methods, a primer is hybridized to one of the strands of the double-stranded nucleic acid template; a new strand is synthesized from the primer by a polymerase; synthesis is paused or blocked at specific sites; and the detection of these pauses or blockages in polymerisation gives information on the sequence of the said nucleic acid.

It has now been discovered according to the invention that it is possible to exploit the physical parameters associated with this blockage to obtain information on the sequence of the double-stranded nucleic acid. More precisely, the inventors have found that it is possible to physically locate on the said double-stranded nucleic acid molecule the site where the replication pause or blockage occurs; the specific physical position of the pause or blockage then provides information on the sequence of the said double-stranded nucleic acid.

The present invention stems from the observation that it is possible to measure the physical distance between the two ends of a partially denatured double-stranded nucleic acid molecule when the said molecule is under tension. In a sequencing-by-synthesis process, the progression of a replication fork is associated with the unwinding of the double-stranded nucleic acid molecule, leaving behind two free ends which are joined at the fork. When the replication is blocked at a specific site, the double-stranded nucleic-acid molecule is blocked in a conformation where the the two strands in front of the replication fork are still annealed, while the two parental strands behind the fork are separated. The inventors have now found that it is possible to measure the physical distance between the two separated ends of the said double-stranded nucleic acid molecule, when the said double-stranded nucleic acid molecule is under tension. The physical position on the said double-stranded nucleic acid molecule of the site where the pause or blockage of replication occurs can then be deduced from the said distance, resulting in some information about the sequence of the said double-stranded nucleic acid molecule.

Thus, the method of the invention relates to a method for the determination of a nucleic acid sequence, said method comprising the steps of:
a) denaturing a double-stranded nucleic acid molecule corresponding to the said nucleic acid sequence
b) hybridizing a single-stranded nucleic acid molecule ("the primer") with the said denatured double-stranded nucleic acid molecule;
c) applying a tension to the hybridized primer/double-stranded nucleic acid molecule obtained in b);
d) incubating the hybridized primer/double-stranded nucleic acid molecule obtained in step b) with a polymerase in conditions which will lead to at least one pause in replication; and
e) determining the position of the said pause in replication with respect to one end of the double-stranded nucleic acid.

By 'denaturation', it is herein meant the process of strands separation of a double-stranded nucleic acid molecule occurring when most of the hydrogen bonds between the said strands are broken. The denaturation process yields a denatured nucleic acid molecule, by which it is herein meant the two separated complementary strands resulting from the denaturation of a double-stranded nucleic acid molecule. By 'renaturation', it is herein referred to the process by which two separated complementary strands reform through hybridization into a double helix. As used herein, 'hybridization' is the process of establishing a non-covalent, sequence-specific interaction between two or more complementary strands of nucleic acids into a single hybrid.

There are several possibilities known to the skilled person to denature the nucleic acid. In a most preferred manner, the two strands are separated by submitting them to a physical force. For example, the free ends of the said double-stranded nucleic acid may be pulled apart, thus rupturing all the bonds between the paired bases, and opening the double-stranded nucleic acid.

In this type of sequence determination method, it can be advantageous, in order to facilitate re-pairing, to arrange for the free ends of the double-stranded DNA (i.e. the ends which are not attached to supports) to be joined to one another covalently or quasi-covalently before pulling apart. In a preferred embodiment, the double-stranded nucleic acid molecule is a hairpin. In another preferred embodiment, the 5' end of one strand is directly joined covalently to the 3' end of the other strand. If it is desired that the double-stranded nucleic acid be represented diagrammatically in the context of the present invention, it is possible to liken it to a "zip fastener", which is opened (or closed): the denaturation of the double-stranded nucleic acid is the unzipping, the renaturation the rezipping.

The single-stranded nucleic acid of the invention can be in particular a DNA or an RNA molecule, either natural or modified. The terms "deoxyribonucleic acid" and "DNA" as used herein mean a polymer composed of deoxyribonucleotides. The terms "ribonucleic acid" and "RNA" as used herein mean a polymer composed of ribonucleotides. The said single-stranded nucleic acid may also be made of modified nucleotides, such as locked nucleic acid (LNA), which are nucleotides in which the ribose moiety is modified with an extra bridge connecting the 2' oxygen and 4' carbon, or peptide nucleic acid (PNA), wherein the backbone is composed of repeating N-(2-aminoethyl)-glycine units linked by peptide bonds.

The invention applies to any type of double-stranded nucleic acid. Most often, the double-stranded nucleic acid will be DNA, but it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of the at least partial re-pairing of two single strands obtained from samples of different origins. Finally, the invention also applies to the secondary structures of a sole single-stranded DNA or of a sole single-stranded RNA.

In a typical configuration, the double-stranded nucleic acid molecules may be specifically anchored on two solid substrates (e.g. microscope slide, micropipette, microparticle). One of the ends may be attached directly or indirectly to a surface, while the other end is attached directly or indirectly to a movable surface. In this embodiment, a tension is applied on both ends of the double-stranded nucleic acid when the supports are moved away. When the tension is higher than a threshold value, the two strands are separated and the nucleic acid molecule is denatured. The tension applied is preferentially above or equal to 15 pN; it is more preferentially above or equal to 16 pN; it is even more preferentially above or equal to 17 pN; in a very much preferred aspect, it is above or equal to 18 pN. This force may vary with temperature, nucleotide type and buffer, but the skilled person will easily adapt the said force with regard to these parameters in order to obtain the separation of the two strands.

In a preferred embodiment of the invention, the double-stranded nucleic acid is denatured by applying a tension higher than a threshold value. Incubating the denatured double-stranded nucleic acid with a single-stranded nucleic acid (the "primer") leads to hybridization of the said single-stranded primer. Preferentially, the sequence of the single-stranded nucleic acid molecule is complementary to at least part of the sequence of the double-stranded nucleic acid molecule.

When the tension is decreased to around an intermediate value, the two strands of the denatured double-stranded nucleic acid can rehybridize. To obtain rehybridization of the said two strands, a tension of between 10 and 12 pN is applied; more preferentially it is 12 pN; even more preferentially, it is 11 pN; still more preferentially, it is 10 pN. According to the invention, the polymerase activity is active under these conditions of tension, resulting in primer extension by nucleotide incorporation into a new strand. Most preferably, the double-stranded nucleic acid is a hairpin. As used herein, chaipin' means a double helix wherein the 5' end of one strand is physically linked to the 3' end of the other strand through an unpaired loop. The said physical link can be either covalent or non covalent. Preferentially, the said physical link is a covalent bond. Thus, a hairpin consists of a double-stranded stem and an unpaired single-stranded loop. In a hairpin, the ends of the two strands which are not engaged in the loop are free and can thus be pulled apart. This results in the unpairing of the double stranded nucleic acid, thus yielding a denatured double stranded nucleic acid molecule. It is possible to open completely a hairpin double-stranded nucleic acid molecule by pulling on each end of the said nucleic acid molecule with a force higher than a threshold value. When the tension applied to the molecule is decreased to an intermediate value, the nucleic acid molecule self-rehybridizes to reform a hairpin. Under this intermediate tension, a new strand is produced by the polymerase activity of the enzyme, until a blockage is encountered. According to the invention, determining the position of the said blockage in replication with respect to one end of the double-stranded nucleic acid gives information on the sequence of the said double-stranded nucleic acid.

Using a hairpin makes it possible, in particular, to perform cycles of pairing and unpairing and thus to improve the signal/noise ratio.

For the purpose of the invention, the loop can be of any length comprised between 0 and 60 nucleotides. It is believed that a loop region of at least about 4 or 5 nucleotides is needed to form a stable hairpin. However, it is also possible to perform the invention with loops of a much shorter length. Indeed, the inventors have found that in some embodiments of the invention it may be advantageous to use a hairpin which loop consists of 0 nucleotides. In this case, the 3' end of one strand is directly and physically linked to the 5' end of the other strand. Techniques allowing the free ends of double-stranded nucleic acid to be joined together are known, and some will be described in greater details in what follows.

By determination of the blockage, it is herein meant the determination of the physical parameters associated with the blockage. The most useful of these parameters is the position of the blockage on the double-stranded nucleic acid molecule, said position corresponding to the position of the last incorporated nucleotide in the newly synthesized single-strand. Indeed, the inventors have found that the position on the stretched double-stranded nucleic acid at which the pause in renaturation occurs can be precisely determined: the use of hairpin affords the skilled person to determine the physical distance between the two free ends of the hairpin at any time during the denaturation/renaturation process.

By 'free end' it is herein meant the end of one strand which is not covalently linked to an extremity of the other strand; as explained above, these free ends may each be bound to a different surface. For example, one of these surfaces may be movable, whilst the other may be motionless. The skilled person will thus easily realize that, in order to measure the distance between the free ends of the hairpin double-stranded nucleic acid, it is possible to simply measure the distance between the two surfaces.

This distance is maximal ($z_{high}$ at a force ($F_{open}$), which is higher than the threshold value mentioned above) when the hairpin molecule is completely denatured, since the hairpin nucleic acid is then completely extended; it is minimal ($z_{low}$ at a force ($F_{test}$) which corresponds to the intermediate value discussed above)) when the said hairpin molecule is completely renatured. It is advantageous to perform all length comparisons at the same force $F_{test}$, so that the single stranded nucleic acid has the same elastic properties. Using the delay in loop closing the skilled user can measure $z_{high}$ ($F_{test}$).

Figure 1:
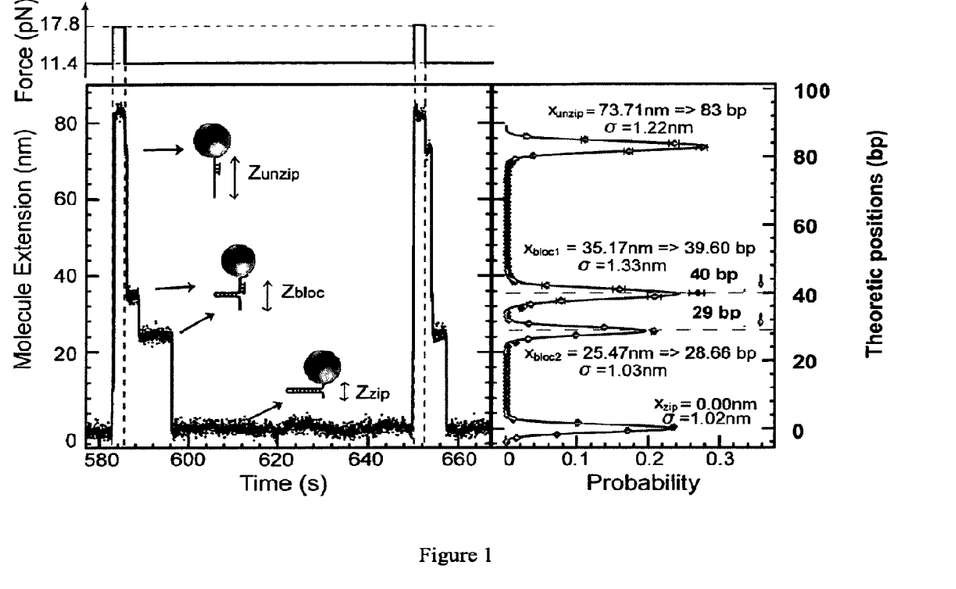
Figure 2:
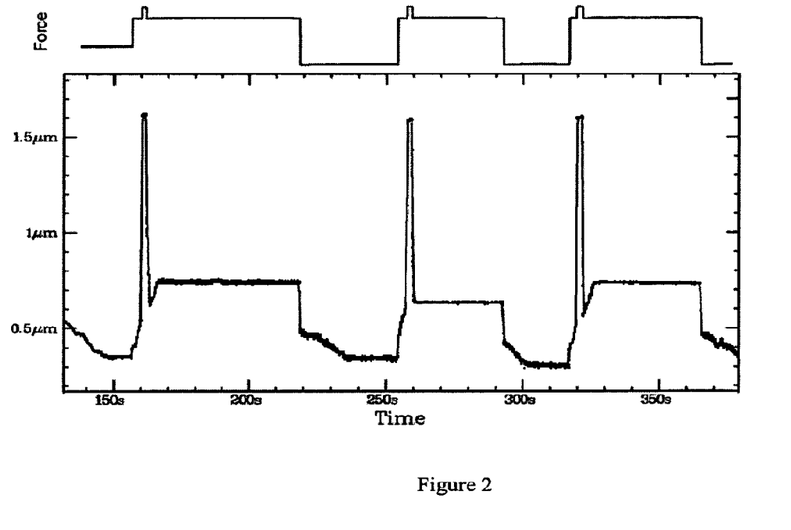
Figure 3:
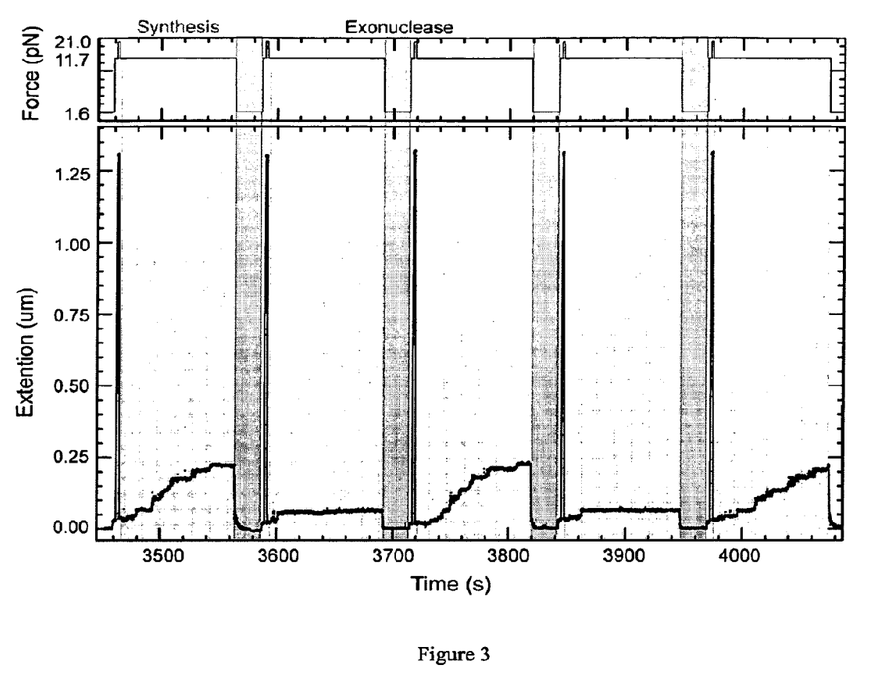
Figure 4:
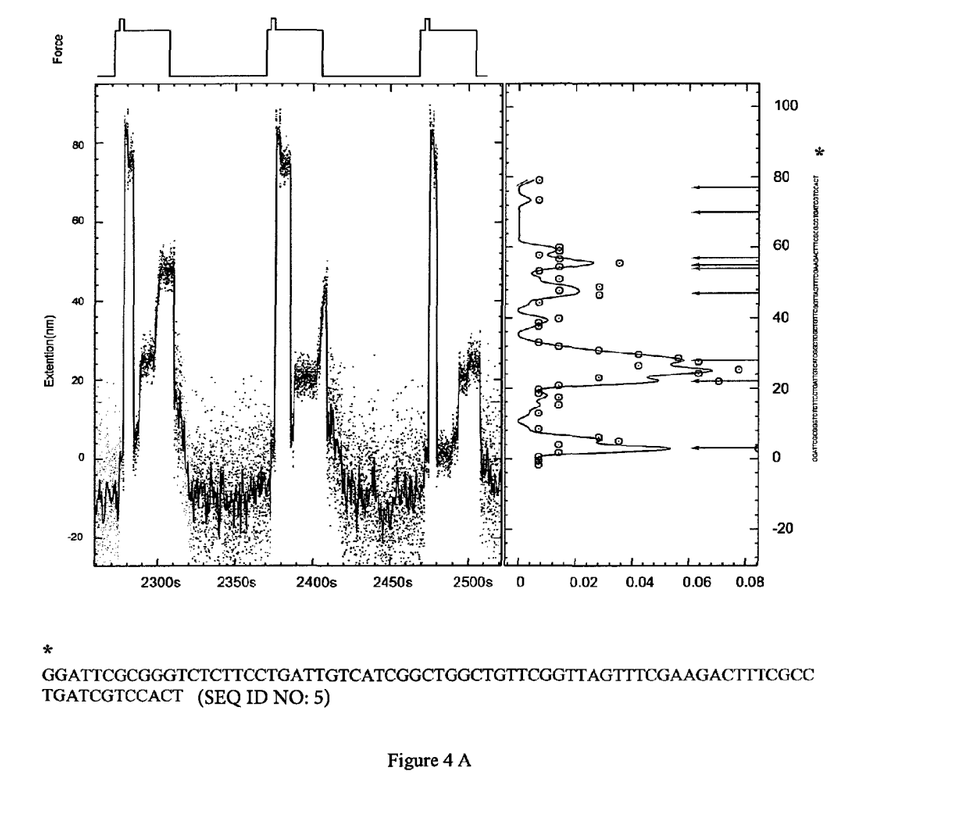
FIG. 4A: Real-time record of synthesis on a 83 bp single molecule hairpin with T4 DNA polymerase (dTNP =dGNP =dCNP =33 µM, dATP =20 nM, clamp and clamp loader) in commercial buffer (5X Reaction Buffer: 335 mM Tris-HCl (pH 8.8 at 25° C.), 33 mM MgCl$_2$, 5 mM DTT, 84 mM (NH4)2SO4, Fermentas; fermentas.com/en/ products/all/modifying-enzymes/mesophilic-polymerases/ ep0064-t4-dna-polymerase). At high force (~21pN), the peak of the curve shows the existence of hairpin sample and could be used to hybridize a primer if needed. At middle force (~11.7 pN), the rising edge of the curve shows the processive synthesis of a new complementary strand by the T4 DNA polymerase, while the transient pause corresponds to the position where a dATP is needed. At low force (~1.6 pN), the falling shows the cleavage of the newly-synthesized strand, due to the activation of the exonuclease activity of the T4 DNA polymerase. This synthesis and cleavage cycle is repeatable. The position histogram of these transient pauses is deduced similarly as previously described in FIG. 1 and base calls are indicated (arrows). The true sequence of the template is shown on the right side of the figure.
FIG. 4B: There are two ways to measure the extension change. First, we can use the Zzip as reference; alternatively, we can also use the position of the hairpin loop as reference.
Figure 5:
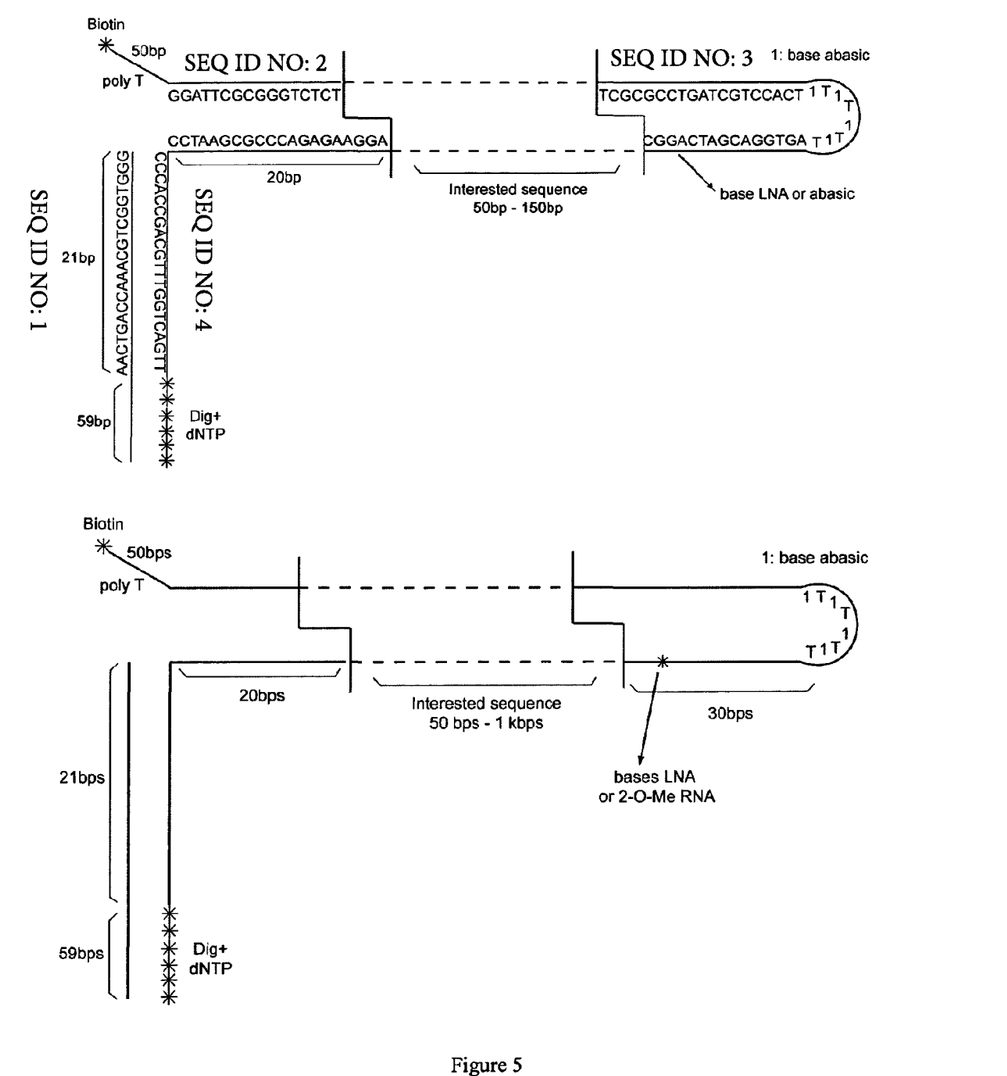

When the replication is blocked at a specific site, the double-stranded nucleic-acid molecule is blocked in a conformation where the two strands in front of the replication fork are still annealed, while the two parental strands behind the fork are separated. The distance between the two free ends when the replication process is temporarily or permanently paused can be measured: as expected, this distance z is comprised between $z_{high}$ and $z_{low}$ (all z being measured with $F=F_{test}$). It is immediately clear that the distance z varies with the localization on the hairpin molecule of the point where the replication fork is paused or blocked. If the said replication fork is paused at a sequence which is located close to the free ends of the hairpin, the distance $z_{pause}$ will be minimal. On the other hand, if the said replication fork is blocked at a sequence corresponding to a part of the hairpin which is close to the unpaired loop, the distance z will be maximal (FIG. 1). The pause can be observed during the polymerase induced unwinding of a hairpin under a tension $F_{test}$. If replication proceeds at a force $F_{open}$ (for which the hairpin is open) until it is blocked, the replication blockage can be observed upon reducing the force to $F_{test}$ which allows for the strands to rezip up to the blockage point.

It is possible to correlate precisely a physical distance on a double-stranded nucleic acid molecule with a number of bases. For example, a distance of 1 nm corresponds to the distance spanned by two nucleotides (1 bp) in a nucleic acid under a 10 pN force. The exact calibration versus force is given by the elasticity of single stranded nucleic acid. Therefore, by simply measuring the distance between the two free ends of the double-stranded nucleic acid molecule under tension, it is possible to determine precisely where the renaturation is blocked.

Thus, in one embodiment, the method of the invention relates to a method for the determination of a nucleic acid sequence, said method comprising the steps of:

a) denaturing a double-stranded nucleic acid molecule corresponding to the said nucleic acid sequence ;

b) hybridizing a single-stranded nucleic acid molecule ("the primer") with the said denatured double-stranded nucleic acid molecule;

c) applying a tension to the hybridized primer/double-stranded nucleic acid molecule obtained in b);

d) incubating the hybridized primer/double-stranded nucleic acid molecule obtained in step b) with a polymerase in conditions which will lead to at least one pause in replication; and e) determining the position of the said pause in replication with respect to one end of the double-stranded nucleic acid, wherein the distance between the two ends of the double-stranded molecule is determined when the replication process is blocked. Preferentially, the distance between the two ends of the said molecule is determined when the molecule is completely denatured. Even more preferentially, the two distances are compared and the position of the blockage is determined.

As used herein, "polymerase" refers to an enzyme that catalyzes the polymerization of nucleotides (i.e., the polymerase activity). Generally, the enzyme will initiate synthesis at the 3' end of the primer annealed to a polynucleotide template sequence, and will proceed toward the 5' end of the template strand. "DNA polymerase" catalyzes the polymerization of deoxynucleotides, while "RNA polymerase" catalyses the polymerization of ribonucleotides. The polymerase according to the invention is either a processive polymerase or non-processive polymerase. A processive enzyme catalyses multiple rounds of a reaction on a denatured double-stranded nucleic acid template, while the enzyme stays bound to the said template. As understood herein, a polymerase will be processive i.e. will stay bound to the denatured double-stranded nucleic acid template for at least 25 nucleotides, at least 50 nucleotides, at least 100 nucleotides, usually at least 500 nucleotides, and may be processive for at least 1000 nucleotides or more. Polymerases according to the invention include RNA-dependent RNA polymerases, DNA-dependent RNA polymerases, DNA-dependent DNA polymerases, RNA-dependent DNA polymerases (reverse transcriptase) and the like. Many such enzymes are known in the art. According to the invention, the said polymerase is capable of synthesizing nucleic acids when the force applied to the double-stranded nucleic acid template is at an intermediary value, i.e. comprised between 10 and 12 pN or at high forces for which the hairpin is completely unfolded Preferably, a polymerase with a 3'-5' exonuclease activity is used in the method of the invention. As used herein, "3'-5' exonuclease activity" refers to the capability of an enzyme to remove incorporated nucleotides from the 3' end of a DNA polymer. Examples of such enzymes include e.g. T4 DNA Polymerase, T7 DNA Polymerase, DEEP VENT DNA polymerase, E. coli polymerase III, Phi29 DNA Polymerase, E. coli DNA Polymerase I, E. coli DNA Polymerase I, Klenow Fragment, Phusion® High Fidelity DNA Polymerase, Phusion® Hot Start High Fidelity DNA Polymerase, Phire® Hot Start DNA Polymerase, 9°Nm DNA Polymerase, Herpes Simplex Virus Type 1 DNA Polymerase. In a preferred embodiment, the polymerase of the invention can be switched from a polymerase-active mode to a 3'-5' exonuclease-active mode by decreasing the force applied to the double-stranded nucleic acid molecule under a minimal value. Preferably, the said minimal value is 7 pN; more preferably, the said minimal value is 6 pN; even more preferably, the said minimal value is 5 pN.

Even more preferably, the said polymerase has, in addition, a strand displacement activity under an intermediate tension, e.g. when a force between 10 and 12 pN is applied to the double-stranded hairpin. By "strand displacement", it is herein meant the ability for the polymerase to displace the downstream nucleic acid during synthesis. The inventors have found in particular that the T4 DNA Polymerase and the T7 DNA polymerase, which are not known to have any strand displacement activity in test tube conditions, i.e. in conditions where no tension is applied to the double-stranded template, are able to remove the downstream nucleic acid during polymerisation when the double-stranded hairpin is under a force ≥10 pN. The T4 DNA Polymerase and T7 DNA Polymerase are thus particularly suited for carrying out the method of the invention. "T4 DNA Polymerase" and "T7 DNA Polymerase" herein refer to both the monomeric enzyme and the holoenzyme.

The method according to the invention comprises a replication step which is carried out under conditions which will lead to at least one pause in the replication process. Preferably, the double-stranded nucleic acid molecule is submitted to a tension during the replication step. More preferably, the said tension is around an intermediate value, i.e. the said tension is comprised between 10 and 12 pN. The said pause can be caused by any of the means known to the person of skills in the art. Sequencing-by-synthesis method wherein the synthesis of the new strand is blocked have been widely used in the art. Any such method can be adapted for the purpose of the present invention. For example, the polymerase may be a nucleotide-sensitive, processive enzyme, which is then contacted with the denatured double-stranded nucleic acid template in a reaction mix which is rate-altering for the processive movement of the enzyme for a specified nucleotide. For example, the said reaction mix comprises a pool of deoxy-nucleotides (dNTP) where one of the bases is present at a very low concentration. In that case, each time the polymerase encounters the complement of the said nucleotide, it pauses until the low concentration nucleotide diffuses into position. The positions of the pauses along the molecule thus reveal the positions of the scarce nucleotide in the synthesized strand and allows the skilled person to identify the position of the corresponding base in the sequence (Greenleaf and Block, *Science,* 313: 801, 200; U.S. Pat. No. 7,556,922). Alternatively, it is possible to use dideoxynucleotides (ddNTPs) in addition to the normal deoxynucleotides (dNTPs) found in DNA. Dideoxynucleotides are essentially the same as nucleotides except they contain a hydrogen group on the 3' carbon instead of a hydroxyl group (OH). These modified nucleotides, when integrated into a sequence, prevent the addition of further nucleotides. This occurs because a phosphodiester bond cannot form between the dideoxynucleotide and the next incoming nucleotide, and thus the DNA chain is terminated. Therefore, incorporation of one ddNTP will cause the polymerase reaction to stop, since no nucleotide can be added after the said ddNTP. The position of the blockage along the molecule thus reveals the position of incorporation of the ddNTP in the synthesized strand and allows the skilled person to identify the position of the corresponding base in the sequence. The position of each pause or blockage can then be determined by the method of the invention, i.e. by measuring the physical distance between the two free ends of the molecule. Besides, it is also possible to use nucleoside triphophate (NTPs) instead of ddNTPs. The difference is, incorporation of one NTP will only transiently pause the process of polymerase, generating a pattern similar to the first proposed example mentioned here.

The method of the invention may be used for direct sequencing of an unknown nucleic acid. In a preferred embodiment, a processive enzyme is used to synthesize from a known single-stranded nucleic acid (a primer) a sequence of increasing extension complementary to one of the hairpin strands, thereby effectively unwinding the double-stranded hairpin maintained under a moderate tension (e.g. in the range of 5 to 13 pN). In this embodiment, polymerisation is initiated by opening the double-stranded hairpin by transiently increasing the force to $F_{open}$ in the presence of a single-stranded primer. $F_{open}$ is a tension higher than the threshold value required for completely opening the double stranded hairpin. This results in the hybridization of the primer to the double-stranded hairpin. In a next step, the force is set to $F_{elongation}$ ($\leq F_{open}$) in order to enable the polymerase to synthesize a new strand (in a strand displacement mode or not). $F_{elongation}$ is preferably set at an intermediate tension lower than $F_{open}$ (the threshold value required for complete opening of the double stranded hairpin), said intermediate tension allowing for replication by the polymerase. Preferably, the said intermediate value is comprised between 10 and 12 pN. Under a tension equal to $F_{elongation}$, the polymerase synthetizes a new strand at a sustained rate until a pause or a blockage occurs. The enzyme activity thus leads to the production of an extended complementary single-stranded nucleic acid molecule.

In the strand displacement configuration, the said polymerase can be switched between its two modes of operation, i.e. exonuclease activity and elongation, by adjusting the force applied on the hairpin.

In a preferred embodiment, the elongation process is stopped before the polymerase reaches the loop. This can be achieved by various means. For example, the insertion of non conventional bases a few nucleotides ahead of the loop will stop the polymerase. The same effect can be achieved with a double-stranded binding domain of a protein located just before the loop.

In a further preferred embodiment, the force ($F_{exo}$) applied to the hairpin molecule is decreased under a minimal value, e.g. 5 pN, after the elongation process is blocked. This allows the polymerase to switch to its exonuclease activity and disassemble the strand which has just been synthesized. This process stops when the whole strand is completely disassembled. Alternatively, the disassembly process is stopped when the enzyme is stalled, e.g. when encountering a roadblock, such as a modified nucleotide in the primer. In such a case, it may be necessary to use an enzyme to eject the newly-synthesized strand. As examples of suitable enzymes, one may cite e.g. helicases, including a UVrD helicase, a recBCD helicase, *E. coli* UvrD helicase, Tte-UvrD helicase, T7 Gp4 helicase, RecBCDhelicase, DnaB helicase, MCM helicase, Rep helicase, RecQ helicase, PcrA helicase, T4 UvsW helicase, SV40 large T antigen helicase, Herpes virus helicase, yeast Sgs1 helicase, DEAH_ATP-dependent helicases and Papillomavirus helicase E1 protein and homologs thereof, and exonucleases, including snake venom phosphodiesterase, spleen phosphodiesterase, Bal-31 nuclease, *E. coli* exonuclease I, *E. coli* exonuclease VII, Mung Bean Nuclease, S1 Nuclease, an exonuclease activity of *E. coli* DNA polymerase 1, an exonuclease activity of a Klenow fragment of DNA polymerase 1, an exonuclease activity of T4 DNA polymerase, an exonuclease activity of T7 DNA polymerase, an exonuclease activity of Taq DNA polymerase, an exonuclease activity of DEEP VENT DNA polymerase, *E. coli* exonuclease III, $\lambda$ exonuclease and an exonuclease activity of VENTR DNA polymerase.

Disassembly of the strand which has just been synthesized provides the opportunity to repeat the whole process, i.e. the synthesis of a strand under a tension superior to a threshold, e.g. 10 pN, with the polymerase pausing e.g. every time it encounters the complement of the rare nucleotide or stopping if it incorporates a ddNTP or a NTP. If the primer has been expelled during the disassembly step, synthesis will be preceded by a step of opening the hairpin and closing it back so that a primer can hybridized. Increasing the force above 10 pN will switch back the polymerase in the elongation mode and a new pausing pattern may be recorded. Repeating the synthesis/disassembly cycle thus makes it possible to record several pausing patterns with the same rare nucleotide. This leads to an improved signal/noise ratio, allowing the obtention of a sequence of a higher quality with fewer errors. Alternatively the replication step can be conducted in the presence of ddNTP at a high force where the hairpin is completely open. In that case blockages resulting from ddNTP incorporation can be detected upon lowering the force to $F_{test}$.

Once sufficient statistics have been recorded the procedure is repeated with a shortage of another nucleotide or another ddNTP. After the said procedure has been repeated with each nucleotide, the positions of all the nucleotides in the strand are compiled together, thus yielding the complete sequence of the original double-stranded nucleic acid molecule.

Implementation of the method of the invention has been made possible, in particular, by the existence of devices designed for probing real-time nucleic acid interaction at the single-molecule level. Such a device is described for example in U.S. Pat. Nos. 7,052,650 and 7,244,391. The apparatus described therein uses magnetic traps to apply a picoNewton scale force on a micron-sized super-paramagnetic bead. Briefly, the said apparatus comprises an optical microscope, magnets and a PC. The double-stranded nucleic acid molecules are anchored at multiple points at one end to a motionless element, e.g. a surface, and at the other end to a movable surface, in this case a magnetic bead. Magnets are provided for acting on the bead. In particular, the magnets may be used for pulling the bead away from the surface. However, the implementation of the method of the invention is not restricted to the above apparatus. Any device which allows one to fully extend and then refold a molecule of double stranded nucleic acid, whilst monitoring at the same time the extension of the said molecule can be used to implement the method of the invention. For example, optical tweezers may be used; they require however prior force calibration and are not easily parallelized for high throughput measurements. Further drawbacks are the lack of total torsional control of the nucleic acid and the possible local heating of the solution by the focussed laser which may alter the hybridization conditions.

The double stranded nucleic acid is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation.

The bead-nucleic acid assembly is injected in a fluidic chamber the surface of which has been treated such as to bind the other labeled end of the molecule (for example a surface coated with anti-Dig to bind the Dig-labeled end of the nucleic acid). The beads are thus anchored to the surface via a nucleic acid hairpin, see FIG. 1a. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the nucleic acid molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback loop on the trapping beam.

To exert a constant force on a bead, the use of the hydrodynamic drag generated by a flow around the bead has been described, but it usually yields a low spatial accuracy (>100 nm). The preferred embodiment uses a magnetic trap to pull on super-paramagnetic beads anchored to a surface by a nucleic acid hairpin as described above. In this configuration, small magnets placed above the sample are used to apply a constant force on the anchored bead, whose position can be determined with <1 nm accuracy (depending on the pulling force and the dissipation due to hydrodynamic drag) In every case one notices that the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, some molecules in solution (such as proteins or complementary oligonucleotides of DNA, RNA, LNA or PNA) have bound to the stretched single stranded nucleic acid, these molecules will block the rezipping of the hairpin when the force is lowered to below 11 pN. The principle of the assay is thus to switch between two forces: a large one $F_{open}$ to open the hairpin and a smaller one $F_{test}$ used to allow re-zipping and to measure the extension of the molecule at transient blockages. The blocking position is related to the sequence by a linear relation between full extension and the blocked one.

For best accuracy, the full extension is preferably measured at the test force $F_{test}$. This is achieved by designing the hairpin loop such that it requires a fraction of a second to refold once the force is reduced from $F_{open}$ to $F_{test}$.

In order to attach nucleic acids to surfaces or supports, use may be made of any one of the techniques known in the field. Essentially, the nucleic acid becomes anchored directly to the support, for example the micro-bead, which involves a functionalization of this surface, for example by coating it with streptavidin, a COOH group, and the like, capable of reacting with the functionalized end of the nucleic acid.

Such methods necessitate, in general, functionalizing the nucleic acid, especially the 3' and 5' ends, that is to say grafting appropriate chemical groups onto them. It is, moreover, preferable to join the other two free ends of the molecule by a loop in order to prevent the strands from dissociating at the end of the operation, so that the latter can be repeated if appropriate. For this purpose, different procedures may be adopted.

The simplest is to functionalize, using synthetic oligonucleotides, one of the ends of a double-stranded nucleic acid with two different functions (biotin and amine, for example), which permit anchoring to two different pretreated surfaces. The two strands at the other end may be joined using a partially paired synthetic nucleotide in the form of a loop. In this way, a paired, single-stranded nucleic acid, i.e. a hairpin, is produced from a double-stranded nucleic acid. The advantage of this method lies in its capacity to functionalize a heterogeneous population of large nucleic acid fragments (as are obtained by fractionation of a gene or chromosome), which can then be analyzed simultaneously. In this case, the nucleic acid sample is fractionated using two (or more) restriction enzymes, which enables a subpopulation to be obtained with two different restriction sites at its ends which are similar over all the fragments. This enables the two ends to be treated differently (for example by joining one end to an oligonucleotide in the form of a loop possessing the appropriate restriction site at its end). The drawback of this method lies in the steric interference between the two adjacent functional groups, which can make coupling to the surfaces difficult. To solve this problem, it can be advantageous to add at each free end of the hairpin molecule a "spacer" sequence of bases, to the end of which a functional group is then added; the two spacer sequences are non-complementary, affording each functional group enough space to bind to its dedicated surface. More advantageously, the sequence of each spacer sequence is designed in order to use single-stranded sequencing primers of known sequence in the sequencing method of the invention. The addition of a loop and/or spacers to the double-stranded nucleic acid molecules can be performed with any of the methods commonly used in molecular biology. These methods are well known to the person skilled in the art and there is thus no need to detail them here.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of nucleic acid may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a nucleic acid functionalized with digoxigenin may be anchored thereto. This represents merely a sample of the many possible anchoring techniques. Among the attachment and anchoring techniques, there should also be mentioned, for example, the techniques described in Patent EP 152 886 using an enzymatic coupling for the attachment of DNA to a solid support such as cellulose.

Patent EP 146 815 also describes various methods of attachment of DNA to a support.

Similarly, patent application WO 92/16659 proposes a method using a polymer to attach DNA.

Naturally, the nucleic acid may be attached directly to the support but, where necessary, especially with a view to limiting the influence of the surfaces, the nucleic acid may be attached at the end of an inert arm of peptide or other nature, as is, for example, described in Patent EP 329 198.

The practice of the invention employs, unless other otherwise indicated, conventional techniques or protein chemistry, molecular virology, microbiology, recombinant DNA technology, and pharmacology, which are within the skill of the art. Such techniques are explained fully in the literature. (Sec Ausubel et al., Current Protocols in Molecular Biology, Eds., John Wiley & Sons, Inc. New York, 1995; Remington's Pharmaceutical Sciences, 17th ed., Mack Publishing Co., Easton, Pa., 1985; and Sambrook et al., Molecular cloning: A laboratory manual 2nd edition, Cold Spring Harbor Laboratory Press—Cold Spring Harbor, NY, USA, 1989).

The examples below will enable other features and advantages of the present invention to be brought out.

LEGENDS OF THE FIGURES

FIG. 1 Principle of detection of the hybridization of oligo-nucleotides to their complementary sequence on a hairpin DNA. The hairpin DNA anchoring the bead to the surface (a) is momentarily unzipped by increasing the force pulling on the bead to a value above 16 pN. In that phase the complementary fragment in solution hybridizes to its target on the opened DNA hairpin, thus preventing the rezipping of the hairpin (b) when the force is reduced back to its initial value. The hairpin refolding presents four plateaus occuring at well defined extensions but with variable duration. The top plateau at 73.71 nm is associated with the 83 bp fully opened hairpin at $F_{test}$, while the bottom one corresponds to the hairpin completely refolded. The two intermediate plateaus at 25.47 nm and 35.17 nm occur because two oligos have been placed in the solution. From these change in extension ($z_{high}$-z) it is possible to deduce where along the hairpin the complementary sequence has paired. Here according to their positions the blocks coincide with location 28.66 bp and 39.60 bp in very good agreement with their expected positions at 29 bp and 40 bp. The plateau positions are better estimated by fitting Gaussian to the histogram obtained from several opening/closing cycles (here ~20 cycles).

FIG. 2: Illustration of single molecule Sanger sequencing. Real-time record of synthesis on a 1.2 kbps single molecule hairpin with T4 DNA polymerase (dTNP=dGNP=dCNP= 500 µM, dATP =5 µM, ddATP =400 µM, clamp and clamp loader) in a commercial buffer (5X Reaction Buffer: 335 mM Tris-HCl (pH 8.8 at 25° C.), 33 mM MgCl$_2$, 5 mM DTT, 84 mM (NH$_4$)$_2$SO$_4$, Fermentas; fermentas.com/en/ products/all/modifying-enzymes/mesophilic-polymerases/ ep0064-t4-dna-polymerase). At high force, the peak of the curve shows the existence of hairpin sample. At middle force, the rising curve shows the processive synthesis of a new complementary strand by the T4 DNA polymerase, while the plateau represents the pause occurring when one ddNTP is incorporated. At low force, the falling edge of the curve shows the exonuclease activity removing the strand just synthesized. These synthesis and exonuclease phases may be repeated in cycles.

FIG. 3: Illustration of sequencing based on unbalanced dNTP concentration. Real-time record of synthesis on a 1.2 kbps single molecule hairpin with T4 DNA polymerase (dTNP =dGNP =dCNP =33µM, dATP =20 nM, clamp and clamp loader) in commercial buffer (5X Reaction Buffer: 335 mM Tris-HCl (pH 8.8 at 25° C.), 33 mM MgCl$_2$, 5 mM DTT, 84 mM (NH$_4$)$_2$SO$_4$, Fermentas; fermentas.com/en/ products/all/modifying-enzymes/mesophilic-polymerases/ ep0064-t4-dna-polymerase). At high force (~21 pN), the peak of the curve shows the existence of hairpin sample and could be used to hybridize a primer if needed. At middle force (~11.7 pN), the rising edge of the curve shows the processive synthesis of a new complementary strand by the T4 DNA polymerase, while the transient pause corresponds to the presents when a dATP is needed. At low force (~1.6 pN), the falling shows the cleavage of the newly-synthesized strand, due to the activation of the exonuclease activity of the T4 DNA polymerase. This synthesis and cleavage cycle is repeatable.

FIG. 4A-B: Detection of the sequencing based on unbalanced dNTP concentration to their complementary sequence on a hairpin.

FIG. 5. Illustration of hairpin design. The DNA fragment of interest is ligated with a DNA loop (with abasic and LNA bases) and two partially complementary DNA fragments (one ssDNA with Biotin on the end, one dsDNA with Dig at extremity), which eventually forms a hairpin that can be bound to a super-paramagnetic bead covered with strepta- vidin (DYNAL) while the other extremity to a glass cover- slip treated with anti-dig.

EXPERIMENTAL EXAMPLES

DNA Preparation

A double-strand (ds)DNA fragment of unknown sequence and of a size comprised between a few tens and a few thousands base pairs, is ligated at one of its extremities to a DNA loop. Its other extremity is ligated to a dsDNA fragment allowing for the binding of its two strands to differently coated surfaces. For example, the free 3' end of one strand can be labeled with biotin allowing binding to streptavidin coated beads, whereas the 5' end on the opposite strand can be labelled with digoxigenine allowing its bind- ing to surfaces coated with an anti-Dig antibody. This end-labelling can be done by various ways known to the man of the art, such as the use of terminal transferase to add biotin (or dig) modified nucleotides or hybridization with suitably labelled oligo-nucleotides.

Force Stretching Apparatus

This DNA construct is incubated for a few minutes in a solution of adequate beads (for example streptavidin coated ones) to which it binds by one of its labelled (for example biotin) ends. The beads can be transparent if optical tweezers are later used for manipulation or magnetic if one uses magnetic traps or tweezers for manipulation.

The bead-DNA assembly is injected in a fluidic chamber the surface of which has been treated such as to bind the other labelled end of the molecule (for example a surface coated with anti-Dig to bind the Dig-labelled end of the DNA). The beads are thus anchored to the surface via a DNA-hairpin, see FIG. 1a. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the DNA molecule anchoring the beads to the surface various techniques have been described. The pre- ferred embodiment uses a magnetic trap to pull on super- paramagnetic beads anchored to a surface by a DNA hairpin as described above. In this configuration, small magnets placed above the sample are used to apply a constant force on the anchored bead, whose position can be determined with <1 nm accuracy (depending on the pulling force and the dissipation due to hydrodynamic drag). In this series of experiments, the apparatus described in U.S. Pat. Nos. 7,052,650 and 7,244,391 was used. In addition, unless otherwise indicated, the experiments reported here were performed in 25 mM Tris pH 7.5, 150 mM KAc, 10 mM $MgCl_2$, 0.2% BSA. In every case, the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, binding of a molecule in solution (such as a protein or complementary oligo-nucleotides of DNA, RNA, LNA or PNA) to the stretched single stranded (ss)DNA occurred, this molecule will transiently block the rezipping of the hairpin when the force is lowered to below 11 pN. The principle of the assay is to switch between two forces: a large one $F_{open}$ to open the hairpin and a smaller one $F_{test}$ used to allow re-zipping and to measure the extension of the molecule at transient block- ages. The blocking position is related to the sequence by a linear relation between full extension and the blocked one. For best accuracy, the full extension is preferably measured at the test force $F_{test}$. This is achieved by designing the hairpin loop such that it requires a fraction of a second to refold once the force is reduced from $F_{open}$ to $F_{test}$.

The Hybridization Position of an Oligo-nucleotide Can Be Measured with a Basepair Resolution By measuring the extension of the DNA molecule (the distance of the bead to the surface) during one of these rezipping pauses, it is possible to determine the position of the blockage with a nanometer precision (1 nm corresponds to the distance spanned by two nucleotides (1 bp) in a ssDNA under a 10 pN force). The unzipping configuration displays the largest ratio of extension to basepair (in dsDNA the ratio is only 0.34 nm per bp).

The accuracy of this measurement is limited by two noise contributions:

The accuracy of the measuring method,

The brownian motion of the bead.

Different techniques can be used to measure the vertical position of the bead. One of the simplest relies on video microscopy (U.S. Pat. Nos. 7,052,650 and 7,244,391). The results in FIG. 1 where obtained with this method, typical resolution reaches 1 nm for a 1 second averaging. Other methods with better resolution have been demonstrated, such as laser illumination with PSD sensors that reaches 0.1 nm in resolution (Greenleaf and Block, *Science,* 313: 801, 2006) and evanescent wave illumination (Singh-Zocchi et al., *Proc Natl Acad Sci USA.,* 100(13): 7605-7610, 2003 , Liu et al., *Biophys J.,* 96(9): 3810-3821, 2009).

The intrinsic limitation in resolution is given by the brownian fluctuations of the bead pulling on a ssDNA molecule. $<x^2>=4k_BT \, \Delta f \, (6\pi\eta r)/k^2_{ssDNA}(F)$ where $k_{ssDNA}(F)$ is the stiffness of a ssDNA molecule, $k_B$ is Boltzman constant, T the absolute temperature, $\eta$ the viscosity of water, r the bead's radius and $\Delta f$ is the frequency range of the measurement. $k_{ssDNA}(F=10 \text{ pN})=0.05/Nb$ (N/m), where Nb is the number of bases of the ssDNA. For the 84 bp hairpin this leads to 0.04 nm of noise over 1 second ($\Delta f=1$ Hz) averaging. The larger noise in FIG. 1 ($\sigma$~1 nm) is essentially due to the measuring device, not the intrinsic fluctuations. The intrinsic brownian noise increases with the size of the hairpin: a 1200 bp hairpin leads to a noise of 0.6 nm when averaging over 1 second.

Diagnostics and Sequencing By Mechanical Detection of Polymerization.

We have shown that the T4 DNA polymerase can replicate a DNA hairpin when the force is high enough to sufficiently destabilize the fork ($F_{test}$). Like in the classical Sanger sequencing, the incorporation of a specific ddNTP will prevent further elongation of the nascent strand by the T4 DNA polymerase. In our method, this blockage can be easily identified, as shown in FIG. 6. Upon lowering the force, the exonuclease activity of the T4 DNA polymerase is activated and the enzyme excises the newly-synthesized strand. Thus, by repeated cycles of synthesis and cleavage, the molecule (hairpin) can be sequenced by identifying the blockage positions first in the presence of ddATP, and then of each of the other ddNTPs, i.e. ddTTP, ddCTP, and ddGTP.

Similarly, the double-stranded hairpin molecule can be sequenced in a buffer comprising a deficit of one of the four dNTPs compared to the others, i.e. this dNTP is present at a very low concentration as compared to the others. Thus, whenever the T4 DNA polymerase, during polymerization, reaches a position requiring the addition of the limiting nucleotide, a transient pause occurs, as exemplified on FIG. 7. As described hereabove, the newly-synthesized brand can be excised by lowering the force, which results in the activation of the exonuclease activity of the enzyme. Thus, by repeated cycles of synthesis and cleavage, the molecule (hairpin) can be sequenced by identifying the pause positions first in the presence of low concentrations of dATP (for example), and then in turn of each of the other dNTPs, i.e. dTTP, dCTP, and dGTP.

The invention claimed is:

1. A method for detecting blockage of the renaturation of a hairpin molecule, said method comprising:
   a) providing a nucleic acid hairpin molecule consisting of a double-stranded stem and a single-stranded loop, wherein 5' and 3' ends of the nucleic acid hairpin molecule are bound to different surfaces;
   b) applying a force to one of the surfaces such that it is moved away from another of the surfaces, thereby yielding a completely denatured hairpin molecule;
   c) hybridizing a known single-stranded nucleic acid primer to the completely denatured hairpin molecule;
   d) extending the primer with a polymerase, thereby generating a nucleic acid molecule complementary to the completely denatured hairpin molecule;
   e) reducing the force applied to allow renaturation of the completely denatured hairpin molecule in the presence of the nucleic acid molecule complementary to the completely denatured hairpin molecule; and
   f) detecting blockage of the renaturation of the completely denatured hairpin molecule in step e) due to generation of the nucleic acid molecule complementary to the completely denatured hairpin molecule.

2. The method of claim 1, wherein steps a)-f) are repeated.

3. The method of claim 1, wherein the force is reduced to less than or equal to 12 pN.

4. The method of claim 1, wherein the force is reduced to less than or equal to 11 pN.

5. The method of claim 1, wherein the force is reduced to less than or equal to 10 pN.

6. The method of claim 1, wherein the nucleic acid hairpin molecules are made by replicating RNA molecules.

7. The method of claim 1, wherein said one of the surfaces is a magnetic bead.

8. The method of claim 7, wherein the force is a magnetic force.

9. The method of claim 1, wherein the force in step b) is above or equal to 15 pN.

10. The method of claim 1, wherein said extending the primer with a polymerase occurs in a reaction mix comprising a pool of dNTPs, wherein one of the dNTPs in the pool is present at a low concentration as compared to the other dNTPs in the pool.

11. The method of claim 1, wherein said extending the primer with a polymerase occurs in a reaction mix comprising a pool of nucleotides comprising dNTPs and one ddNTP.

12. The method of claim 1, further comprising disassembling the nucleic acid molecule complementary to the completely denatured hairpin molecule after step f).

13. The method of claim 12, wherein steps a)-f) are repeated after said disassembling the nucleic acid molecule complementary to the completely denatured hairpin molecule.

* * * * *